(12) United States Patent
Wang

(10) Patent No.: US 9,493,824 B2
(45) Date of Patent: Nov. 15, 2016

(54) UNIVERSAL REFERENCE DYE FOR QUANTITATIVE AMPLIFICATION

(75) Inventor: Yan Wang, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 576 days.

(21) Appl. No.: 13/328,154

(22) Filed: Dec. 16, 2011

(65) Prior Publication Data

US 2012/0164690 A1 Jun. 28, 2012

Related U.S. Application Data

(60) Provisional application No. 61/423,932, filed on Dec. 16, 2010, provisional application No. 61/432,209, filed on Jan. 21, 2011, provisional application No. 61/508,453, filed on Jul. 15, 2011.

(51) Int. Cl.
*C12Q 1/68* (2006.01)

(52) U.S. Cl.
CPC .................................. *C12Q 1/6851* (2013.01)

(58) Field of Classification Search
None
See application file for complete search history.

(56) References Cited

U.S. PATENT DOCUMENTS

| | | | |
|---|---|---|---|
| 5,736,333 A | 4/1998 | Livak et al. | |
| 5,928,927 A | 7/1999 | Cheng et al. | |
| 7,166,478 B2 | 1/2007 | Stavrianopoulos et al. | |
| 7,553,959 B2 | 6/2009 | Stavrianopoulos et al. | |
| 7,776,567 B2 | 8/2010 | Mao et al. | |
| 2004/0009586 A1 | 1/2004 | Oldham et al. | |
| 2004/0072335 A1* | 4/2004 | Boege et al. | 435/287.2 |
| 2006/0024743 A1* | 2/2006 | Mathies et al. | 435/6 |
| 2008/0187916 A1 | 8/2008 | Ikonomi et al. | |
| 2008/0305481 A1 | 12/2008 | Whitman et al. | |
| 2009/0253142 A1 | 10/2009 | Allawi et al. | |
| 2010/0015629 A1 | 1/2010 | Gupta et al. | |
| 2010/0015630 A1 | 1/2010 | Gupta et al. | |
| 2010/0233710 A1 | 9/2010 | McDougall et al. | |
| 2010/0276580 A1 | 11/2010 | Sharaf et al. | |
| 2010/0291583 A1 | 11/2010 | Exner et al. | |
| 2012/0258500 A1* | 10/2012 | Cheng | 435/91.2 |

FOREIGN PATENT DOCUMENTS

| | | |
|---|---|---|
| EP | 2192198 A1 | 6/2010 |
| EP | 2217719 | 8/2010 |
| WO | 2009/053679 A1 | 4/2009 |

OTHER PUBLICATIONS

Hot Start It™ (USB Corporation, 2007, p. 1-6).*
Kubu et al. (Biotechniques, 2008, 44(2):275-277).*
International Preliminary Report on Patentability for PCT Application No. PCT/US2011/065617, mailed Apr. 4, 2012.
International Search Report for PCT Application No. PCT/US2011/065617, 26 pages, mailed Apr. 4, 2012.
Supplementary European Search Report from EP 11848622.4, dated Nov. 27, 2014.
ActiveMotif: "Antibodies for the study of nuclear function." Jul. 12, 2010 (26 pages) retrieved from the internet at www.activemotif.co.jp/pdf/AM/_abs_brochure_web_100712.pdf on Nov. 14, 2013.

* cited by examiner

*Primary Examiner* — Stephanie K Mummert
(74) *Attorney, Agent, or Firm* — Kilpatrick Townsend and Stockton LLP

(57) ABSTRACT

Universal reference dye mixtures for quantitative amplification, and uses thereof, are provided.

18 Claims, 3 Drawing Sheets

UNIVERSAL REFERENCE DYE FOR QUANTITATIVE AMPLIFICATION

CROSS-REFERENCE TO RELATED PATENT APPLICATIONS

The present application claims benefit of priority to each or U.S. Provisional Application No. 61/423,932, filed Dec. 16, 2010; U.S. Provisional Application No. 61/435,209, filed Jan. 21, 2011; and U.S. Provisional Application No. 61/508,453, filed Jul. 15, 2011, each of which are incorporated by reference for all purposes.

BACKGROUND OF THE INVENTION

Real-time detection of DNA amplification during polymerase chain reaction (PCR) provides quantitative data for amplified DNA target sequences by relating the number of temperature cycles during thermal cycling needed to reach the concentration threshold (Ct) of the target sequence to the amount of target DNA present at the start of the PCR process. Thus, accurate and reproducible determination of the amount of target sequence present can be effected by detecting accurate Ct values. One aspect to determining accurate Ct values is to relate the fluorescent signal generated during thermal cycling to a passive internal reference dye for normalization of signal across samples and correction of well-to-to well optical variation in high-throughput multiwell assays (see, e.g., Real-time PCR, ed. Julie Logan, Kristin Edwards, Nick Saunders, 2009; Wong, M L and Medrano, J F, *Biotechniques*, 39:75-85, 2005 and Gehua et al. *Can. J. Microbiol.*, 53:391-397, 2007). Since excitation optics vary between different instrument platforms, the optimal passive reference dye concentration must be matched to a specific real-time thermal cycler.

5- and/or 6-carboxy-X-rhodamine (e.g., available commercially as ROX™) is commonly used as a passive reference dye in a number of instruments. The passive (not interacting with components of a nucleic acid amplification reaction, not participating in 5'-exonuclease-induced fluorescent signal generation (if used), not affecting amplification reaction efficiency, etc.) reference, 5- or 6-carboxy-X-rhodamine dye, provides an internal reference to which the reporter dye signal can be normalized. This signal normalization allows one to correct for fluorescent fluctuations due to changes in concentration or volume. Normalization of the reporter dye signal results in increased data precision and reproducibility among replicate reactions. In some 'normalization' calculations the fluorescence emission intensity of the reporter dye or other fluorescent signal indicating amplicon quantity is divided by the fluorescence emission intensity of a passive reference dye (e.g., 5- or 6-carboxy-X-rhodamine dye) to obtain a ratio for the normalized reporter or $R_n$. The difference between the values of the baseline and the template-containing sample equals the delta $(\Delta)R_n$, indicating the magnitude of signal generated by the sample under those specific PCR conditions. Absolute or relative expression can be determined on the basis of an assigned threshold and the number of cycles needed to cross that threshold ($C_t$, $C_p$ or $C_q$).

Due to differences in design of thermal cyclers, some instruments employ a high concentration of 5- or 6-carboxy-X-rhodamine dye for normalization while others employ low concentration. On a high-Rox instrument, such as AB7900, the light source is laser-based with excitation at 480 nm. When the Rox dye, which has maximum absorbance at 580 nm, is used for passive normalization, it is not efficiently excited by the 480 nm laser. To compensate for the low efficiency of excitation of the Rox dye and to generate sufficient signal for proper normalization, very high concentration of the Rox dye has to be used. Thus this instrument is referred to as the "high-Rox" platform. While many other real-time platforms detect signal in different channels, the AB7900 collects signals in different bins, with a set of bins designated for ROX.

On a low-Rox instrument such as AB7500, a broad-spectrum light source is used, which is then divided into 4 excitation wavelength through the use of filters for the corresponding channels. The emission is detected within each designated channel. Therefore, the Rox dye can be maximally excited in the "Rox" channel and generating adequate signal for normalization without requiring high concentration of the Rox dye. Thus, such instrument and alike are referred to as the "low-Rox" platforms. Typically, the Rox concentration used by a "high-Rox" platform is about 10-fold higher than that used by a "low-Rox" platform.

BRIEF SUMMARY OF THE INVENTION

The present invention provides for a reaction mixture for signal normalization in a real-time polymerase chain reaction (PCR) amplification of a target nucleic acid wherein the mixture is compatible for use in both (a) a real-time PCR amplification system employing high passive reference dye concentration for the normalization and (b) a real-time PCR amplification system employing low passive reference dye concentration for the normalization, wherein the mixture comprises a plurality of passive reference dyes that produces fluorescent signals independent of the amplification reactions.

In some embodiments, the mixture comprises a first passive reference dye (or other fluorescent agent) having a Stokes-shift, wherein the first passive reference dye (or other fluorescent agent) is at a concentration sufficient for use in low concentration passive reference dye normalization, wherein the first passive reference dye (or other fluorescent agent) has a first passive reference dye (or other fluorescent agent) excitation wavelength maximum (also known as an absorbance maximum) and a first passive reference dye (or other fluorescent agent) emission wavelength maximum; and a second passive reference dye (or other fluorescent agent) having a Stokes-shift that is greater than the Stokes-shift of the first passive reference dye, wherein the second passive reference dye (or other fluorescent agent) has an emission wavelength maximum approximately the same as the first passive reference dye (or other fluorescent agent) emission wavelength maximum, and an excitation wavelength maximum significantly different than the first passive reference dye (or other fluorescent agent) excitation wavelength maximum.

In some embodiments, the second passive reference dye (or other fluorescent agent) has a Stokes-shift of at least about 60 nm.

In some embodiments, the first passive reference dye comprises 5- and/or 6-carboxy-X-rhodamine, or an analog thereof. In some embodiments, the mixture comprising a 5- and/or 6-carboxy-X-rhodamine dye; and a second passive reference dye having a Stokes-shift of at least about 60 nm, wherein the second passive reference dye has an emission wavelength maximum of about 620 nm. In some embodiments, the mixture comprising a 5- and/or 6-carboxy-X-rhodamine dye; and a second passive reference dye having a Stokes-shift of at least about 60 nm, wherein the second passive reference dye has an emission wavelength maximum of about 590 nm.

In some embodiments, the mixture comprises a 5- and/or 6-carboxy-X-rhodamine dye; and a second passive reference dye having a Stokes-shift of at least about 60 nm, wherein the dye has an emission wavelength maximum of about 620 nm.

In some embodiments, the concentration of the 5- and/or 6-carboxy-X-rhodamine dye is less than 100 nM. In some embodiments, the concentration of the 5- or 6-carboxy-X-rhodamine dye is about 10 nM.

In some embodiments, the mixture further comprises one or more of an oligonucleotide primer, one or more deoxynucleoside triphosphates; a buffer, an intercalating fluorescent dye, and a polymerase.

In some embodiments, the mixture further comprises DNA polymerase. In some embodiments, the polymerase is complexed with an antibody. In some embodiments, the polymerase is chemically inactivated but is activated by heating.

In some embodiments, the mixture comprises a reverse transcriptase.

In some embodiments, the second passive reference dye is conjugated to a moiety.

In some embodiments, the second fluorescent dye (i.e., having a Stokes-shift of at least 60 nm) has a excitation wavelength maximum of 460, 470, 480, 490, 500, 510, 520, 530, 540, 550, 560 nm or less.

In some embodiments, the first and/or second passive reference dye having a Stokes-shift is a fluorescent dot (e.g., including but not limited to a quantum dot or a semiconducting polymer dot).

The present invention also provides for methods of performing a real-time quantitative polymerase chain reaction. In some embodiments, the method comprises performing a polymerase chain reaction (PCR) with the mixture as described above or elsewhere herein, wherein the mixture further comprises a biological sample suspected of possibly having a target nucleic acid.

In some embodiments, the PCR is performed with an instrument, or in an amplification method, that does not employ passive reference dye normalization.

In some embodiments, the method further comprises detecting signal from either or both of the 5- or 6-carboxy-X-rhodamine dye and the second passive reference dye (i.e., the dye having a Stokes-shift of at least 60 nm). In some embodiments, the PCR is performed with an instrument, or in an amplification method, that employs the use of high concentration of free 5- or 6-carboxy-X-rhodamine dye for normalization, and the method further comprises detecting signal from the second passive reference dye or both the second passive reference dye and the 5- or 6-carboxy-X-rhodamine dye. In some embodiments, the signal from both the 5- or 6-carboxy-X-rhodamine dye and the second fluorescent dye (i.e., the dye having a Stokes-shift of at least 60 nm) is detected. In some embodiments, the method comprises normalizing the signal for the target nucleic acid in the polymerase chain reaction with the signal from the second passive reference dye or both the second passive reference dye and the 5- or 6-carboxy-X-rhodamine dye.

In some embodiments, the PCR is performed with an instrument, or in an amplification method, that employs the use of low concentration of free 5- or 6-carboxy-X-rhodamine dye for normalization, and the method further comprises: exciting the 5- or 6-carboxy-X-rhodamine dye but not substantially exciting the second passive reference dye (i.e., the dye having a Stokes-shift of at least 60 nm); and detecting signal from the 5- or 6-carboxy-X-rhodamine dye. In some embodiments, the method comprises normalizing signal for the target nucleic acid in the polymerase chain reaction with the signal from the 5- or 6-carboxy-X-rhodamine dye and not from the second passive reference dye.

In some embodiments, the first and/or second passive reference dye having a Stokes-shift is a fluorescent dot.

The present invention also provides for a method of making the reaction mixture as described above or elsewhere herein. In some embodiments, the method comprises mixing the plurality of passive reference dyes, thereby generating the reaction mixture.

In some embodiments, the mixture comprises: a first passive reference dye having a Stokes-shift, wherein the first passive dye has a first passive reference dye excitation wavelength maximum and a first passive reference dye emission wavelength maximum; and a second passive reference dye having a Stokes-shift that is greater than the Stokes-shift of the first passive reference dye, wherein the second passive reference dye has an emission wavelength maximum approximately the same as the first passive reference dye emission wavelength maximum, and an excitation wavelength maximum significantly different than the first passive reference dye excitation wavelength maximum.

In some embodiments, the second passive reference dye has a Stokes-shift of at least about 60 nm.

In some embodiments, the first passive reference dye comprises 5- and/or 6-carboxy-X-rhodamine, or an analog thereof.

In some embodiments, the first passive reference dye comprises a 5- and/or 6-carboxy-X-rhodamine dye or an analog thereof, and the second passive reference dye is a fluorescent dye having a Stokes-shift of at least 60 nm, wherein the second passive reference dye has an emission wavelength maximum of about 620 nm or about 590 nm.

In some embodiments, the mixture further comprises mixing at least one or more of the following with the first and second passive reference dyes: one or more deoxynucleoside triphosphates; one or more of an oligonucleotide primer, one or more deoxynucleoside triphosphates; a buffer, an intercalating fluorescent dye, and a DNA polymerase.

In some embodiments, the mixture comprises a reverse transcriptase.

In some embodiments, the first and/or second passive reference dye having a Stokes-shift is a fluorescent dot.

The present invention also provides for kits for performing a real-time quantitative polymerase chain reaction. In some embodiments, the kit comprises: a first passive reference dye having a Stokes-shift, wherein the first passive dye has a first passive reference dye excitation wavelength maximum and a first passive reference dye emission wavelength maximum; and a second passive reference dye having a Stokes-shift that is greater than the Stokes-shift of the first passive reference dye, wherein the second passive reference dye has an emission wavelength maximum approximately the same as the first passive reference dye emission wavelength maximum, and an excitation wavelength maximum significantly different than the first passive reference dye excitation wavelength maximum.

In some embodiments, the second passive reference dye has a Stokes-shift of at least about 60 nm.

In some embodiments, the first passive reference dye comprises 5- and/or 6-carboxy-X-rhodamine, or an analog thereof.

In some embodiments, the first passive reference dye comprises a 5- and/or 6-carboxy-X-rhodamine dye or an analog thereof, and the second passive reference dye is a fluorescent dye having a Stokes-shift of at least 60 nm, wherein the second passive reference dye has an emission wavelength maximum of about 620 nm or about 590 nm.

In some embodiments, the kit further comprises one or more of: one or more deoxynucleoside triphosphates; one or more of an oligonucleotide primer, one or more deoxynucleoside triphosphates; a buffer, an intercalating fluorescent dye, and a DNA polymerase.

In some embodiments, the mixture comprises a reverse transcriptase.

In some embodiments, the first passive reference dye and the second passive reference dye are contained in different vessels in the kit.

In some embodiments, the first passive reference dye and the second passive reference dye are contained in the same vessel in the kit.

In some embodiments, the first and/of second passive reference dye having a Stokes-shift is a fluorescent dot.

DEFINITIONS

Figure 1:
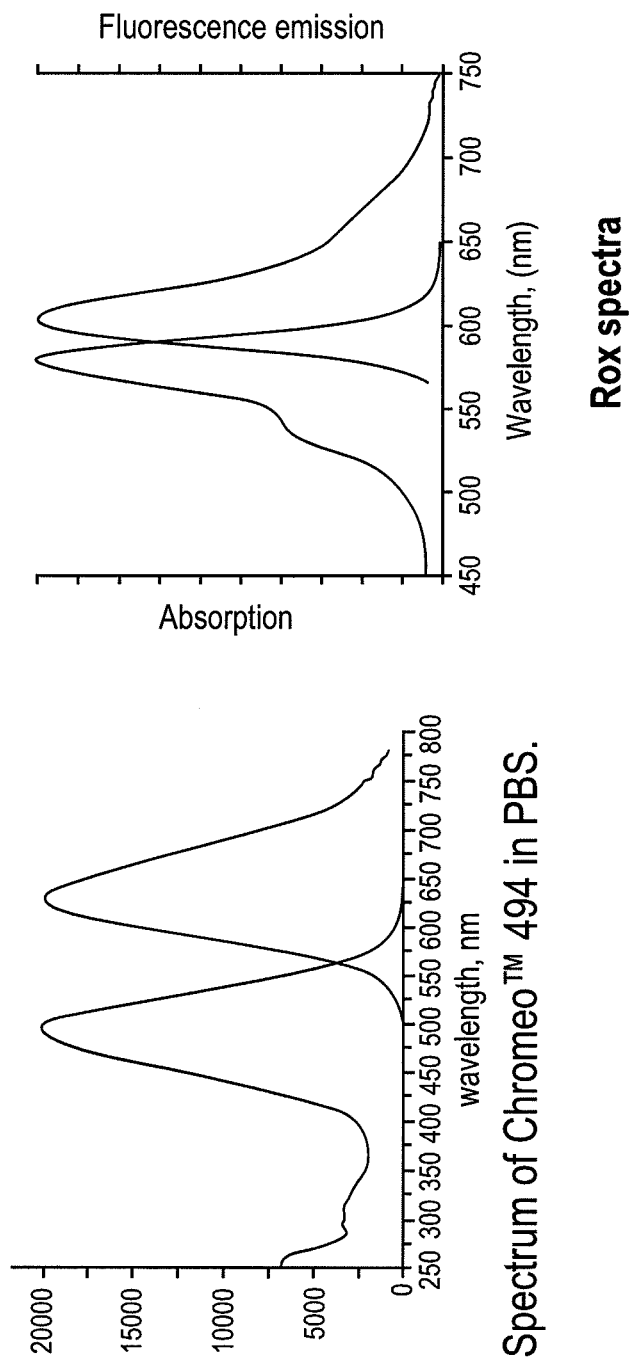
FIG. 1. Excitation and emission spectra of Chromeo 494 and ROX.

A "passive reference dye" refers to a fluorescent dye or dot that does not interact with other components of a polymerase chain reaction. For example, the passive reference dye does not significantly change its signal based on the presence or absence of nucleic acids and does not significantly interact in FRET interactions with another dye in the PCR reaction mixture. The passive reference dye can be, but in many embodiments, is not linked to a nucleic acid. The passive reference dye can have a Stokes-shift, i.e., such that the excitation wavelength maximum and the emission maximum are different.

A "low" passive reference dye (e.g., 5- or 6-carboxy-X-rhodamine dye such as ROX™) concentration, as used herein, is a concentration of a passive reference dye (e.g., 5- or 6-carboxy-X-rhodamine dye or a 5- or 6-carboxy-X-rhodamine dye analog) suitable by itself for use in a low ROX concentration amplification (e.g., qPCR) system. Low 5- or 6-carboxy-X-rhodamine dye concentration instruments ("a qPCR instrument employing a low 5- or 6-carboxy-X-rhodamine dye concentration for normalization") include but are not limited to the Applied Biosystems ABI 7500 or Applied Biosystems ViiA7 or Stratagene MX series real-time PCR systems. Thus, low passive reference dye (e.g., 5- or 6-carboxy-X-rhodamine dye) concentrations are generally less than 100 nM, e.g., 1-10 nM, 10-100 nM, etc.

A "high" passive reference dye (e.g., 5- or 6-carboxy-X-rhodamine dye such as ROX™) concentration, as used herein, is a concentration of a passive reference dye (e.g., 5- or 6-carboxy-X-rhodamine dye such as ROX™ or a 5- or 6-carboxy-X-rhodamine dye analog) suitable for use in a high 5- or 6-carboxy-X-rhodamine dye concentration amplification (e.g., qPCR) system. High 5- or 6-carboxy-X-rhodamine dye concentration instruments ("a qPCR instrument employing the use of a high 5- or 6-carboxy-X-rhodamine dye concentration for normalization") include but are not limited to the Applied Biosystems ABI PRISM 7000, 7700, or 7900 or the ABI 7300 Real-Time PCR Systems or the ABI GeneAmp 5700 Real-Time PCR System. Thus, high passive reference dye (e.g., 5- or 6-carboxy-X-rhodamine dye) concentrations are generally more than 100 nM, e.g., 100-300 nM, 300-700 nM, etc.

"An emission wavelength maximum approximately the same as the passive reference dye emission wavelength maximum" refers to an emission wavelength maximum that is with 30 nm, and optionally, 20, 10, 5, 3, or 1 nm of the passive reference dye emission wavelength maximum.

"Significantly different" in the context of excitation wavelengths of dyes, refers to wavelengths sufficiently different that one dye can be excited without exciting a second dye with a significantly different excitation wavelength maximum. In some embodiments, "significantly different" means the two dyes have excitation maxima at least 10, 20, 30, 40, 50, 60, 70 nm, or more apart.

A "solid support" refers to a material or group of materials having a rigid or semi-rigid surface or surfaces. In some embodiments, the solid support takes the form of thin films or membranes, beads, fibers, woven fibers, shaped polymers, particles, and microparticles, including but not limited to, microspheres. A solid support can be formed, for example, from an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Some exemplary functional groups, e.g., carboxylic acid (—COOH), free amine (—NH2), and sulfhydryl (—SH) groups, naturally present on the surface of a carrier can be used for linkage. In case no such functional group is naturally available, a desired functional group, such as a carboxylic acid group, or a moiety known to be a partner of a binding interaction (such as avidin that is capable of binding biotin) may be attached to such solid support. In some embodiments, the solid support is a carboxylated latex or magnetic microsphere.

DETAILED DESCRIPTION OF THE INVENTION

I. Introduction

The present invention provides for a quantitative amplification pre-mixture ("pre-mix") that can be used regardless of whether an amplification instrument or method employs high or low passive reference dye (e.g., 5- or 6-carboxy-X-rhodamine dye) concentrations for normalization of data, or if the instrument or method does not employ passive reference dye (e.g., 5- or 6-carboxy-X-rhodamine dye) normalization at all. Accordingly, the invention provides a universal pre-mix that can be used for any type of real-time instrument or real-time amplification method without further addition of reagents aside from the sample to be tested and, in some embodiments, the primers to be used. Historically, different types of amplification instruments and methods used for quantitative PCR (qPCR) employed use of either high or low 5- or 6-carboxy-X-rhodamine dye concentrations as a passive reference dye for normalization and thus pre-mixes for use in qPCR were not "universal" because the pre-mixes either had low or high concentrations of 5- or 6-carboxy-X-rhodamine dye. If one wanted to use a high 5- or 6-carboxy-X-rhodamine dye concentration instrument with a low 5- or 6-carboxy-X-rhodamine dye concentration pre-mix, additional 5- or 6-carboxy-X-rhodamine dye had to be added to the pre-mix, thereby adding an additional step and possible introduction of error. The present invention provides for a single mix that can be used for either instrument without addition of any reagents aside from the test sample itself and optionally, primers.

The invention provides for an amplification mixture comprising a fluorescent dye with a long Stokes-shift ("a second passive reference dye") as well as a low concentration of the first passive reference dye (e.g., 5- or 6-carboxy-X-rhodamine dye). The fluorescent dye with a long Stokes-shift is selected such that the dye is excited at a wavelength significantly different than that of the first passive reference dye (e.g., 5- or 6-carboxy-X-rhodamine dye has an excitation maximum at ~575 nm), but has an emission wavelength maximum substantially the same as the passive reference dye (5- or 6-carboxy-X-rhodamine dye has an emission wavelength maximum of ~620 nm). The concentration of the fluorescent dye with a long Stokes-shift is determined such that the combined signal of the fluorescent dye with a long Stokes-shift and the first passive reference dye (which can be, but is not limited to, 5- or 6-carboxy-X-rhodamine dye), in the mixture is sufficient for use in high concentration passive reference dye real-time amplification instruments and can be, for example, to subsequently normalize data. When used on a low concentration passive reference dye real-time amplification instrument, the fluorescent dye with a long Stokes-shift will not be excited in the passive reference dye (e.g., 5- or 6-carboxy-X-rhodamine) channel, thus not generating any additional signal in the channel and so can be detected/used for passive reference dye normalization. The signal generated by the low concentration of passive reference dye present in the pre-mix is used for normalization instead. As a result, this pre-mix can be used on both "high-passive reference dye" and "low-passive reference dye" instruments.

II. Pre-Mixtures

The present invention provides for amplification "pre-mixes", i.e., aqueous or reconstituted mixtures of reagents sufficient to be used in amplification with addition of the sample only, or the sample and primers and/or probes, and optionally minimal or no other reagents. As discussed above, the pre-mixes contain a concentration of a fluorescent dye with a long Stokes-shift as described elsewhere herein as well as a low concentration of passive reference dye (including but not limited to, 5- or 6-carboxy-X-rhodamine dye or a 5- or 6-carboxy-X-rhodamine dye analog).

In some embodiments, the passive reference dye (e.g., 5- or 6-carboxy-X-rhodamine dye or 5- or 6-carboxy-X-rhodamine analog dye) is at a concentration of, e.g., 1-10 nM, 10-100 nM. The concentration of the fluorescent dye with a long Stokes-shift will depend on the quantum yield of the particular dye used to generate sufficient signal to meet the need of the instrument platform that employs high Rox concentration for normalization. For example, in some embodiments, the fluorescent dye is Chromeo 494 (carboxylic acid conjugated form) and the concentration is from 1-5 µM.

The pre-mixes can further contain one or more reagents useful and/or required for amplification or detection of the sample. Exemplary possible reagents include, but are not limited to, one or more salt, one or more buffer, one or more nucleic acid polymerase and/or reverse transcriptase, one or more an oligonucleotide primer, as well as other reagents that improve the amplification reaction (including but not limited to sarcosine or heparin). In some embodiments, the mixtures contain all reagents necessary for target amplification, and optionally detection, except for the target nucleic acid itself. In some embodiments, the mixture further includes the target nucleic acid.

In some embodiments, the mixtures of the present invention can include one or more oligonucleotide primer. Oligonucleotide primers useful in the present invention can be any oligonucleotide of two or more nucleotides in length. In some embodiments, PCR primers are about 15 to about 30 bases in length, and are not palindromic (self-complementary) or complementary to other primers that can be used in the reaction mixture. Primers can be, but are not limited to, homopolymers, primers specific to a target RNA template (e.g., a sequence specific primer), or mixtures of random primers. Any primer can be synthesized by a practitioner of ordinary skill in the art or can be purchased from any of a number of commercial venders (e.g., from Boehringer Mannheim Corp., Indianapolis, Ind.; New England Biolabs, Inc., Beverley, Mass.; Pharmacia LKB Biotechnology, Inc., Piscataway, N.J.; Integrated DNA Technology, Coralville, Iowa; Eurogentec, San Diego, Calif.; Sigma Genesys, The Woodlands, Tex.). Optionally, the mixtures can comprise one or more labeled oligonucleotide. Labels can include, for example, fluorescent labels including but not limited to FRET labels. Such labeled oligonucleotides can be useful, for example, for TAQMAN™ amplification as detailed further below. It is to be understood that a vast array of primers can be useful in the present invention, including those not specifically disclosed herein, without departing from the scope or preferred embodiments thereof.

Nucleotide bases useful in the present invention can be any nucleotide useful in the polymerization of a nucleic acid. Nucleotides can be naturally occurring, unusual, modified, derivative, or artificial. Nucleotides can be unlabeled, or detectably labeled by methods known in the art (e.g., using radioisotopes, vitamins, fluorescent or chemiluminescent moieties, dioxigenin). In some embodiments, the nucleotides are deoxynucleoside triphosphates, dNTPs (e.g., dATP, dCTP, dGTP, dTTP, dUTP, α-thio-dNITs, biotin-dUTP, fluorescein-dUTP, digoxigenin-dUTP, 7-deaza-dGTP). dNTPs are also well known in the art and are commercially available venders (e.g., from Boehringer Mannheim Corp., Indianapolis, Ind.; New England Biolabs, Inc., Beverley, Mass.; Pharmacia LKB Biotechnology, Inc., Piscataway, N.J.). In some embodiments, the nucleotides comprise 1, 2, 3, or 4 different deoxynucleoside triphosphates selected from dATP, dCTP, dGTP, dTTP, and dUTP.

The nucleotides of the present invention can be present in any useful concentration. In some embodiments, the nucleotides are present in an amount from about 1 nM to about 1000 nM. In other embodiments, the nucleotide are present in an amount from about 10 nM to about 750 nM. In still other embodiments, the nucleotides are present in an amount from about 100 nM to about 500 nM. One of skill in the art will appreciate that other concentrations of nucleotides are useful in the present invention.

Buffering agents and salts useful in the present invention provide appropriate stable pH and ionic conditions for nucleic acid synthesis, e.g., for DNA polymerase activity. A wide variety of buffers and salt solutions and modified buffers are known in the art that can be useful in the present invention, including agents not specifically disclosed herein. Exemplary buffering agents include, but are not limited to, TRIS, TRICINE, BIS-TRICINE, HEPES, MOPS, TES, TAPS, PIPES, and CAPS. Exemplary salt solutions include, but are not limited to solutions of, potassium acetate, potassium sulfate, potassium chloride, ammonium sulfate, ammonium chloride, ammonium acetate, magnesium chloride, magnesium acetate, magnesium sulfate, manganese chloride, manganese acetate, manganese sulfate, sodium chloride, sodium acetate, lithium chloride, and lithium acetate.

The buffering agents of the present invention can be present in any concentration. In some embodiments, the buffer is present in an amount from about 0.1 mM to about 1000 mM. In other embodiments, the buffer is present in an amount from about 1 mM to about 500 mM. In still other embodiments, the buffer is present in an amount from about 5 mM to about 250 mM. One of skill in the art will appreciate that other concentrations of buffer are useful in the present invention.

The salts of the present invention can be present in any concentration. In some embodiments, the salt is present in an amount from about 0.01 mM to about 1000 mM. In other embodiments, the salt is present in an amount from about 0.1 mM to about 500 mM. In still other embodiments, the salt is present in an amount from about 1 mM to about 100 mM. One of skill in the art will appreciate that other concentrations of salts are useful in the present invention.

One or more of these additives can be incorporated in the present compositions to optimize the generation and replication of nucleic acids from a ribonucleic acid template. Additives can be organic or inorganic compounds. Inhibition-relieving agents useful in the present invention include, but are not limited to, polypeptides such as; human serum albumin, bovine serum albumin (BSA), ovalbumin, albumax, casein, gelatin, collagen, globulin, lysozyme, transferrin, myoglobin, hemoglobin, α-lactalbumin, fumarase, glyceraldehyde-3-phosphate dehydrogenase (GAPDH), amyloglucosidase, carbonic anhydrase, β-lactoglobulin, aprotinin, soybean trypsin inhibitor, trypsinogen, phosphorylase b, myosin, actin, β-galactosidase, catalase, tryptic soy digests, tryptose, lectins, *E. coli* single-stranded binding (SSB) protein, phage T4 gene 32 protein, and the like, or fragments or derivatives thereof. Examples of nonpolypeptide additives include, but are not limited to; tRNA, rRNA, sulfur-containing compounds, acetate-containing compounds, dimethylsulfoxide (DMSO), glycerol, formamide, betain, tetramethylammonium chloride (TMAC), polyethylene glycol (PEG), TWEEN 20 non-ionic surfactant, NP 40, non-ionic surfactant, ectoine, and polyols. Exemplary additives include DMSO, glycerol, formamide, betain, TMAC, PEG, TWEEN 20 non-ionic surfactant, NP 40 non-ionic surfactant, ectoine, polyols, *E. coli* (SSB) protein, Phage T4 gene 32 protein, and BSA.

In addition, the pre-mixes can include agents which provide for detection of the amplification products. For example, the pre-mixes can include appropriate hybridization probes for homogenous real time detection of amplification products. In some embodiments, these probes can be appropriately labeled with fluorescent moieties. Other possible components include additional dyes that bind to double-stranded DNA. In some embodiments, the dye can be SYBR green. One of skill in the art will appreciate that other dyes are useful in the present invention.

DNA polymerases useful in the present invention can be any polymerase capable of replicating a DNA molecule. Exemplary DNA polymerases are thermostable polymerases, which are especially useful in PCR, e.g., thermophilic polymerases. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (Tne), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothermophilus* (Bst), *Sulfolobus acidocaldarius* (Sac), *Sulfolobus solfataricus* (Sso), *Pyrodictium occultum* (Poc), *Pyrodictium abyssi* (Pab), and *Methanobacterium thermoautotrophicum* (Mth), and mutants, variants or derivatives thereof.

Several DNA polymerases are known in the art and are commercially available (e.g., from Boehringer Mannheim Corp., Indianapolis, Ind.; Life Technologies, Inc., Rockville, Md.; New England Biolabs, Inc., Beverley, Mass.; Perkin Elmer Corp., Norwalk, Conn.; Pharmacia LKB Biotechnology, Inc., Piscataway, N.J.; Qiagen, Inc., Valencia, Calif.; Stratagene, La Jolla, Calif.). In some embodiments, the DNA polymerase can be Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, and active mutants, variants and derivatives thereof. It is to be understood that a variety of DNA polymerases can be used in the present invention, including DNA polymerases not specifically disclosed above, without departing from the scope or preferred embodiments thereof.

In some embodiments, the polymerase included in the pre-mix is a hybrid polymerase comprising a polymerase domain and a DNA binding domain. Such hybrid polymerases are known to show an increased processivity. See e.g., U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases.

In one aspect, the hybrid polymerase lacks 3'-5' exonuclease activity. In one embodiment, such hybrid polymerases comprise a double point mutation in the polymerase domain that provides this exonuclease deficiency. A variety of mutations can be introduced into a native polymerase domain to reduce or eliminate 3'-5' exonuclease activity. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Methods of assaying 3'-5' exonuclease activity are well-known in the art. See, e.g., Freemont et al., *Proteins* 1:66 (1986); Derbyshire et al., *EMBO J.* 16:17

(1991) and Derbyshire et al., *Methods in Enzymology* 262: 363 85 (1995). It will be understood that while the above-described mutations were originally identified in one polymerase, one can generally introduce such mutations into other polymerases to reduce or eliminate exonuclease activity. In a specific embodiment, a polymerases of the invention comprise the double point mutation D141A/E143A in the polymerase domain. The phrase "corresponding to a position," in reference to polymerase amino acids, refers to an amino acid that aligns with the same amino acid (e.g., D141 or E143) in a reference polymerase amino acid sequence (e.g., SEQ ID NO:2). Sequence comparisons can be performed using any BLAST including BLAST 2.2 algorithm with default parameters, described in Altschul et al., *Nuc. Acids Res.* 25:3389 3402 (1977) and Altschul et al., *J. Mol. Biol.* 215:403 410 (1990), respectively.

In some embodiments, the DNA binding domain of hybrid polymerases of the invention are from a thermostable organism and provides enhanced activity at higher temperatures, e.g., temperatures above 45° C. For example, Sso7d and Sac7d are small (about 7 kD MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the $T_m$ of DNA by up to 40° C. under some conditions (McAfee et al., Biochemistry 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence.

In further embodiments, hybrid polymerases of use in the present invention are described for example in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. Examples of hybrid polymerase proteins and methods of generating hybrid proteins are also disclosed in WO2004011605, which is hereby incorporated by reference in its entirety for all purposes, and in particular for all teachings related to generating hybrid proteins. Methods for producing polymerases comprising a polymerase domain and a nucleic acid binding domain are described, for example, in U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898.

In some embodiments, the polymerases of the pre-mix are prepared for use in "hot start" methods to decrease the generation of primer dimers and unspecific amplification products at ambient temperatures. A number of hot-start methods are known. These include physical separation of the polymerase, use of nucleic acid additives (i.e. aptamers) to inhibit extension reactions at low temperatures, and modifications to the active site of the polymerase. Often, it may be desirable to use "hot start" polymerases. In a hot-start polymerase, a molecule is typically bound to the enzyme at the active site to inhibit polymerase activity at lower temperatures. The molecule is removed at high temperatures (e.g., at 95° C.) to allow the polymerase to function at the desired point of the process. The molecule can be one or more antibody, peptide, or a small organic molecule. For example, hot-start can be achieved using one or more antibody that binds to a polymerase with high affinity at ambient temperatures in an inhibitory manner. The complex is dissociated in a high temperature preheating step.

A polymerase may also be chemically modified for hot-start. Heat labile blocking groups are introduced into the polymerase, which render the enzyme inactive at room temperature. These blocking groups are removed at high temperature prior to cycling such that the enzyme is activated. Heat labile modifications include coupling citraconic anhydride or aconitric anhydride to lysine residues of the enzyme are known in the art, see e.g., U.S. Pat. No. 5,677,152, which is hereby incorporated by reference in its entirety for all purposes and in particular for all teachings related to hot-start methods.

U.S. Patent Application Publication No. 2003/0119150 also discloses a concept of hot start PCR that employs a thermostable exonuclease and a polymerase. This method is based on preventing primer elongation at low temperatures by introducing chemical modifications at the 3' end of at least one primer. A thermostable exonuclease is used that is inactive at ambient temperatures or below. Upon temperature increase, the exonuclease becomes active and capable of removing the 3' modification of the primer to enable it to participate in the amplification reaction. U.S. 20030119150, which is hereby incorporated by reference in its entirety for all purposes and in particular for all teachings related to hot-start methods, further teaches that when hybridization probes are used for real-time monitoring, e.g., TaqMan hybridization probes, Molecular Beacon oligonucleotides, or two oligonucleotide hybridization methods, the presence of a thermostable exonuclease III requires a suitable blocking method for the 3' end of the detection probe to avoid 3' digestion.

In certain aspects, it may be desirable to include an additional compound as an additive to improve efficiency in amplification reactions, including but not limited to qPCR. Exemplary additives are described in, e.g., PCT WO2010/080910. In some embodiments, the additive is an osmolyte included in an amplification reaction of the invention to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds that are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine. Sarcosine is chemically similar to betaine, a chemical which has been shown to improve conventional PCR (Henke, Nucleic Acids Research, 1997).

In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, and about 300 to about 350 mM osmolytes are used in methods and kits of the invention. In some embodiments, the osmolyte is sarcosine (optionally at the above-listed concentrations).

In some embodiments, particularly in the amplification of low-copy target nucleic acids, efficiency decreases due to the binding of polymerase to non-primed double-stranded nucleic acid targets. Binding of the polymerase to the double-stranded targets will prevent those targets from denaturation, hybridizing to primers, and undergoing an amplification reaction. To improve the specificity of the polymerase for primed templates, in some embodiments methods of the invention utilize heparin. Heparin molecules, which are negatively charged, can be included in the reaction mixture to mimic the electrostatic property of double stranded nucleic acids. The addition of heparin can, without being limited to a mechanism of action, prevent excess polymerase from binding to the double-stranded template until a single-stranded primed-template becomes available. In some exemplary embodiments, heparin is used in methods and kits of the invention at concentrations of about 50 to about 750 pg/µl. In further exemplary embodiments, heparin is used in methods and kits of the invention at concentrations of about 75 to about 700, about 100 to about 600, about 125 to about 500, about 150 to about 400, about 175 to about 300, and about 200 to about 250 pg/µl. Other molecules known in the art can be used in a similar manner to prevent non-specific binding of the polymerase to non-primed double-stranded template.

In some embodiments, the pre-mix comprises one or more reverse transcriptases. In some embodiments, the pre-mix comprises one or more DNA polymerase and one or more reverse transcriptase. Exemplary reverse transcriptases include, but need not be limited to, murine leukemia virus (MLV) reverse transcriptase Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase, MMLV RNase H-reverse transcriptase, and Tth and Tth-like DNA polymerases (which when used in the presence of $Mn^{2+}$ function as reverse transcriptases).

III. Long-Stokes Shift Dyes

Any long Stokes-shift dye can be used according to the invention so long as the dye has an excitation wavelength maximum that significantly differs from that of the passive reference dye (e.g., 5- or 6-carboxy-X-rhodamine dye) and has an emission wavelength maximum that can be detected in combination with the passive reference dye with the same detection channel. Accordingly, the excitation (or absorbance) peak wavelength maximum should peak at less than about 560 nm where 5- or 6-carboxy-X-rhodamine dye is the passive reference dye. In some embodiments, the emission peak wavelength maximum of the long Stokes-shift dye will typically be between 590-630, 590-610, or 610-630, e.g., 615-625, e.g., about 620 nm. The dyes will generally not have significant affinity for nucleic acids. "Dyes" as used in the context of this invention, refer to any fluorescent agent having an excitation and emission wavelength maximum. The dyes, for example, can be fully or partially soluble in aqueous solutions or can be insoluble solids that evenly distribute in aqueous solution (e.g. fluorescent particles).

The long Stokes-shift dye can also be selected such that the excitation wavelength maximum of the long Stokes-shift dye and the passive reference dye are sufficiently different that, if desired, the passive reference dye can be excited without substantially exciting the long Stokes-shift dye. Thus in some embodiments, the long Stokes-shift dye has an excitation wavelength maximum of less than 460, 470, 480, 490, 500, 510, 520, 525, 530, 540, 550, 560 nm, e.g., 470-510, 490-510, 480-500 nm, etc. The particular excitation wavelength maximum can be any wavelength so long as it does not significantly overlap with the excitation wavelength maximum of the passive reference dye, and is compatible with real-time amplification instruments optical design. In some embodiments, the Stokes shift (the difference between the excitation and emission wavelength maximum) of the dye is at least, e.g., 60, 75, 100, 150 nm or more (i.e., at least 5, 10, 25, 50 nm, or more from the passive reference dye excitation wavelength maximum).

An exemplary long Stokes-shift dye is Chrome™ 494, which is commercially available from, for example, Active Motif (Carlsbad, Calif.). Chromeo 494 has the following chemical content: $C_{26}H_{32}N_2O_4$, MW 436.55. Chromeo 494 is excited at around 490 nm but emits at about 620 nm.

Another exemplary long Stokes-shift dye has the following formula:

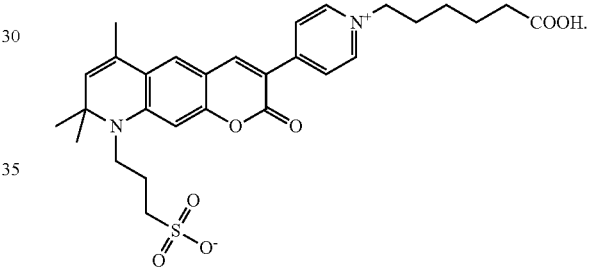

This dye is available commercially as DY-510XL (Dyomics, Jena, Germany). Various modifications of the above-dye are available (e.g., from Dyomics), including, e.g., carboxylic acid ($C_{29}H_{34}N_2O_7S$; MW 554.67), NHS-ester ($C_{33}H_{37}N_3O_9S$; MW 651.74), amino-derivative ($C_{31}H_{41}N_4O_6SCI$; MW 633.21), maleimide ($C_{35}H_{40}N_4O_8S$; MW 676.80), and dUTP ($C_{41}H_{48}N_5O_{20}P3S*4Li$; MW 1083.61) modifications. It is believed such modified dyes as well as other modified versions can be used according to the present invention. For example, the carboxylic acid modified version of the above dye has an adsorption/emission maxima at 509 nm/590 nm.

In some embodiments, the pre-mix will comprise the long Stokes-shift dye in a form free from chemical modification or conjugation. Alternatively, the long Stokes-shift dye can comprise (e.g., can be conjugated to) one or more further chemical moieties so long as they do not significantly affect the excitation or especially the emission wavelength maximum of the dye. Thus, in some embodiments, the long Stokes-shift dye comprises a linker or other moiety. Exemplary moieties include but are not limited to, e.g., an azide, alkyne, carboxylic acid, a NHS-ester, biotin or streptavidin. It will be appreciated that other moieties can also be linked to a dye without significantly affecting the dye's activity as described above. In some embodiments, the long Stokes shift dye is linked to a peptide, oligonucleotide, or other molecule.

In some embodiments, the long Stokes-shift dye is linked to, or is otherwise incorporated with, or contained in a solid support. Exemplary solid supports include but are not limited to beads, particles, and microspheres.

In some embodiments, the long Stokes-shift dye comprises or is a fluorescent dot. Exemplary fluorescent dots include, but are not limited to, quantum dots (see, e.g., U.S. Pat. Nos. 5,482,890, 5,229,320, and 6,326,144) and semi-conducting polymer dots (Pdots), including but not limited to amphiphilic polystyrene semi-conducting polymer (see, e.g., Wu et al., *J Am Chem Soc* 132(43):15410-7 (2010)).

In addition to dyes, other fluorescent agents having a long Stokes shift (i.e., having an excitation wavelength maximum that significantly differs from that of the passive reference dye (e.g., 5- or 6-carboxy-X-rhodamine dye) and having an emission wavelength maximum that can be detected in combination with the passive reference dye with the same detection channel) can also be used as described herein. Other possible agents include, but are not limited to, fluorescent proteins.

The concentration of the particular long Stokes-shift dye or agent used will vary depending on the various parameters, including the quantum yield of the particular dye used. Useful concentrations for the invention can be determined empirically, and can depend, for example, on the precise dye used and the signal strength in the FRET or ROX channel.

IV. Passive Reference Dyes

A number of current commercially available real-time amplification systems employ 5- or 6-carboxy-X-rhodamine dyes as passive reference dyes. Accordingly, in many embodiments, the passive reference dye will be 5- or 6-carboxy-X-rhodamine dye. A commonly used 5- or 6-carboxy-X-rhodamine dye is known as ROX, and is available as the 5-isomer, the 6-isomer, or as a mixture thereof. Alternatively, a 5- or 6-carboxy-X-rhodamine dye analog suitable for 5- or 6-carboxy-X-rhodamine dye normalization (i.e., a dye having excitation and emission properties sufficiently identical to 5- or 6-carboxy-X-rhodamine dye to replace 5- or 6-carboxy-X-rhodamine dye for 5- or 6-carboxy-X-rhodamine dye normalization) can be used. Some 5- or 6-carboxy-X-rhodamine dye analogs are described in, e.g., U.S. Pat. No. 7,736,624. While 5- and/or 6-carboxy-X-rhodamine dye are used to exemplify the invention due to its common usage in PCR as a normalizing dye, it will be appreciated that other passive reference dyes can also be adapted for use in the present invention.

In some embodiments, the pre-mix will comprise the passive reference dye in a form free from chemical modification or conjugation. Alternatively, like the long Stokes-shift dyes described above, the passive reference dye can be chemically modified and/or linked to another molecule, or otherwise incorporated with, or contained, in a solid support so long as the excitation and emission properties are not significantly changed.

V. Methods of Use

As noted above, the pre-mixes of the invention can be used in amplification instruments, methods, and systems that employs (1) high passive reference dye concentrations to normalize results, (2) low passive reference dye concentrations to normalize results, or (3) do not use passive reference dye to normalize data. Thus, no matter what instrument, method, or system one uses, the pre-mixes of the invention are useful.

In situations in which one uses an amplification instrument or platform that employs a high 5- or 6-carboxy-X-rhodamine concentrations to normalize results (e.g., the Applied Biosystems ABI PRISM 7000, 7700, or 7900 or the ABI 7300 Real-Time PCR Systems or the ABI GeneAmp 7500 Real-Time PCR System), the instrument can be calibrated to excite both the 5- or 6-carboxy-X-rhodamine dye and the long Stokes-shift dye. The resulting emissions of the two dyes will be at essentially the same wavelength and as such their combined signal can be detected with a single detector, thereby providing a signal equivalent to a "high 5- or 6-carboxy-X-rhodamine dye concentration" value for use in normalization. For example, when the long Stokes-shift dye is used in conjunction with low Rox on an AB7900 or similarly-configured system, it is optimally excited by the 480 nm laser and generates sufficient signal around the same emission wavelength as the Rox dye for use in normalization. The contribution of the low amount of Rox dye in this circumstance is negligible.

In situations in which one uses an amplification instrument or system that employ a low 5- or 6-carboxy-X-rhodamine dye concentrations to normalize results (e.g., the Applied Biosystems ABI 7500 or Stratagene MX series real-time PCR systems), the instrument can be calibrated to excite the 5- or 6-carboxy-X-rhodamine dye but not the long Stokes-shift dye. For example, the excitation spectrum of the instrument can be set narrowly at or around the excitation of 5- or 6-carboxy-X-rhodamine dye (~620 nm) such that the long Stokes-shift dye, having a different excitation wavelength maximum, is not substantially excited. The resulting emission of the 5- or 6-carboxy-X-rhodamine dye can then be determined and used in normalization without interference of signal from the long Stokes-shift dye. For example, when the long Stokes-shift dye is used in conjunction with low concentration of Rox on an AB7500 or similarly-configured system, although the long stokes-shift is excited in the FAM channel, its emission is not detected because the corresponding detection filter is designed to detect FAM emission, which has the normal stokes-shift of about 50 nm.

Finally, in situations in which one uses an amplification instrument or system that does not employ 5- or 6-carboxy-X-rhodamine dye normalization, the instrument can be calibrated to simply not excite, or not detect, either the long Stokes-shift dye or 5- or 6-carboxy-X-rhodamine dye.

Methods of normalization of amplification data using 5- or 6-carboxy-X-rhodamine dye is well known and therefore are not repeated here.

VI. Kits

The present invention also provides kits for making or using the pre-mixes as described herein. In some embodiments, the kit comprises one vessel comprising the passive reference dye (e.g., 5- or 6-carboxy-X-rhodamine dye or analog thereof) and the long Stokes-shift dye, and optionally other reagents. Other reagents can include, for example, any or all of one or more salt, one or more buffer, one or more nucleic acid polymerase, one or more an oligonucleotide primer, as well as other reagents that improve the amplification reaction (which can include, but are not limited to, sarcosine or heparin).

Alternatively, the kit can be designed such that the end user generates the final pre-mixture. For example, the invention provides for a kit comprising a vessel containing a passive reference dye (e.g., 5- or 6-carboxy-X-rhodamine dye or analog thereof) and a separate vessel containing the long Stokes-shift dye. Optionally, one or both vessels can further comprise any other reagent for use in amplification as described herein, including but not limited to, one or more salt, one or more buffer, one or more nucleic acid polymerase, one or more an oligonucleotide primer, as well as other reagents that improve the amplification reaction (which can include, but are not limited to, sarcosine or heparin). Alternatively, one or more of the additional reagents can be contained in one or more additional vessels.

One can produce a mixture for use in amplification by mixing a passive reference dye (e.g., 5- or 6-carboxy-X-rhodamine dye or analog thereof) with the long Stokes-shift dye, as well as some or all of the one or more salt, one or more buffer, one or more nucleic acid polymerase, one or more oligonucleotide primer, as well as other reagents that improve the amplification reaction (including but not limited to sarcosine or heparin). In some embodiments, the mixture comprises an intercalating fluorescent dye (e.g., SYBR GREEN™). When the mixture is to be used, a nucleic acid sample can also be added to the mixture.

EXAMPLE 1

A dye-based qPCR mix has been developed that can be used on all real-time instrument platforms including the ones that employ high concentration of passive reference dye and the ones that employ low concentration of passive reference dye. The inventive mixture contains a fluorescent dye with a long Stokes-shift mixed with a low concentration of passive reference dye. In a particular embodiment developed, Chromeo 494, the long Stokes-shift dye, is excited at a wavelength that is similar to fluorescein, SYBR Green dye, or EvaGreen dye (e.g. ~490 nm), and emits fluorescence signal in the wavelength range (e.g. ~628 nm) that is similar to passive reference dye (e.g ~605 nm). When the mix is used on an instrument that does not employ passive reference dye normalization, the long Stokes-shift dye and the passive reference dye will not be detected in the FAM channel and thus will not cause any interference. When the mix is used on an instrument that employs high passive reference dye concentration and has a broad excitation spectrum, the long Stokes-shift dye will be excited and emit signals in the passive reference dye channel or bin. The presence of the free passive reference dye will also generate low level of signal in the passive reference dye channel, and the combination of both signals in the passive reference dye channel will be used during normalization. When the mix is used on an instrument that employs low concentration of passive reference dye, which has separate excitation and the corresponding detection filter for each channel, the long Stokes-shift dye will not generate signal, whereas the presence of low concentrations of passive reference dye will generate the appropriate level of signal in the passive reference dye channel to be used for normalization.

Figure 2:
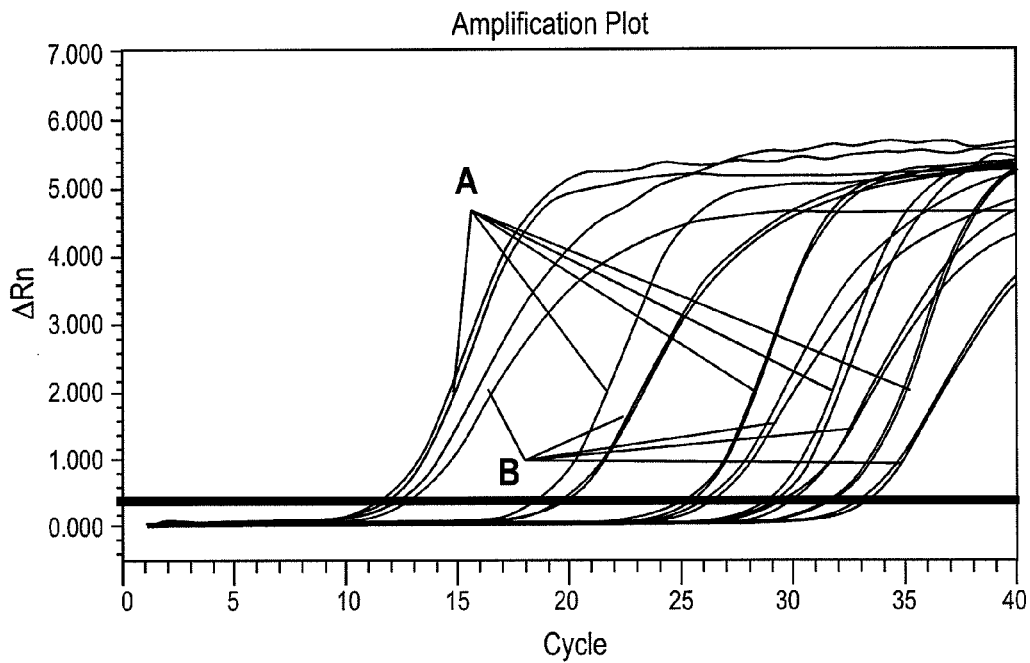
FIG. 2. Performance on AB7900. Compare a SYBR qPCR supermix (A) containing the mixture of Chromeo494 and low concentrations of ROX with the control supermix (B) (Fast SYBR Master Mix, Applied Biosystems) that are formulated to allow proper ROX normalization on both AB7900 and AB7500.
Figure 3:
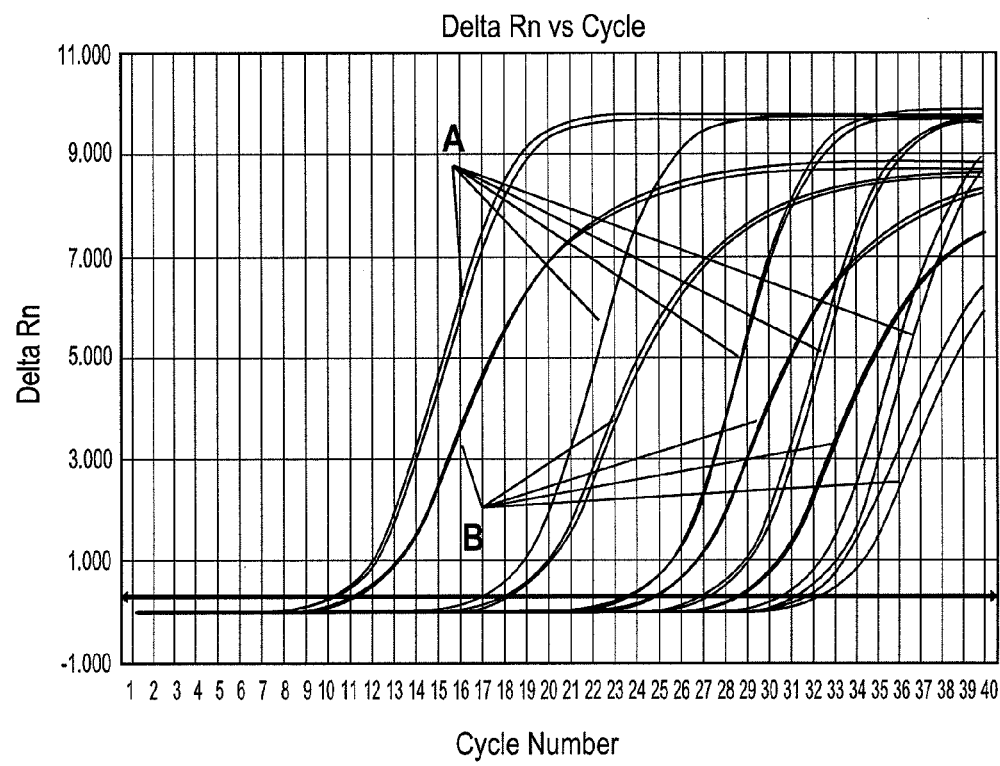
FIG. 3. Performance on AB7500. Compare the same SYBR qPCR supermix (A) and the same control supermix (B) that are used in FIG. 2.

The excitation/emission spectra of an exemplary long Stokes-shift dye, Chromeo 494, and that of the regular Rox reference dye are shown in FIG. 1.

qPCR performance data of a SYBR Green qPCR mix containing Chromeo 494 (carboxylic acid conjugate) and the passive reference dye on AB 7900, an instrument that employs high Rox concentration for normalization, and the same supermix on AB7500, an instrument that employs low Rox concentration for normalization are shown in FIG. 2 and FIG. 3, respectively.

Figure 4:
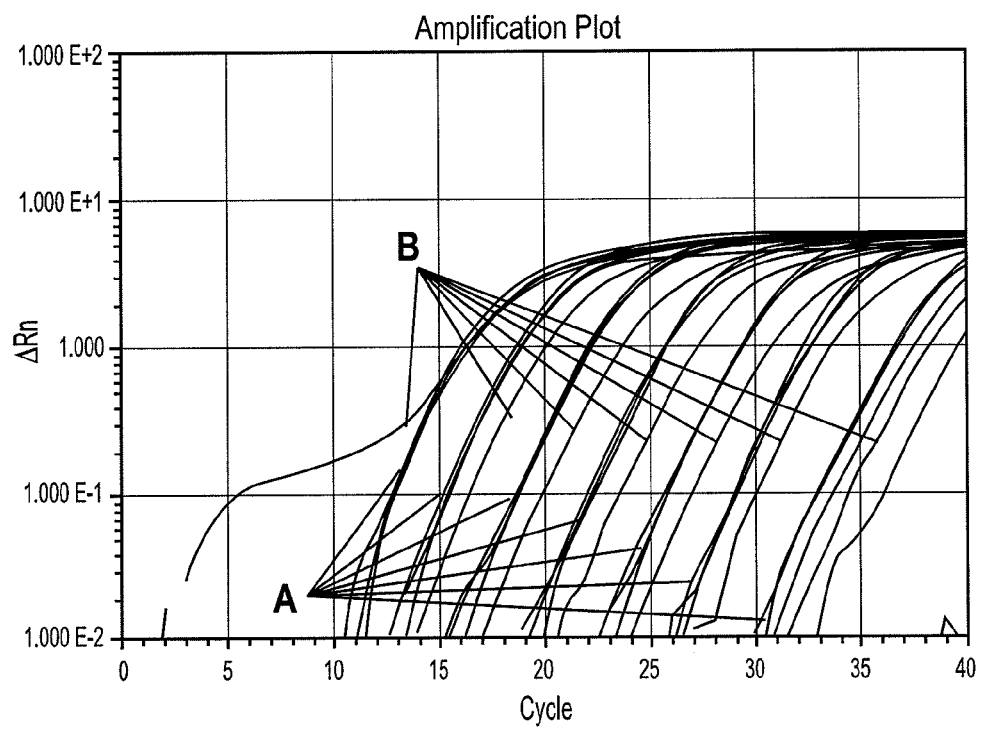
FIG. 4. Performance on AB7900. Compare a SYBR qPCR supermix (A) containing the mixture of DY-510XL dye and low concentrations of ROX with the same control supermix (B) as in FIG. 3.
Figure 5:
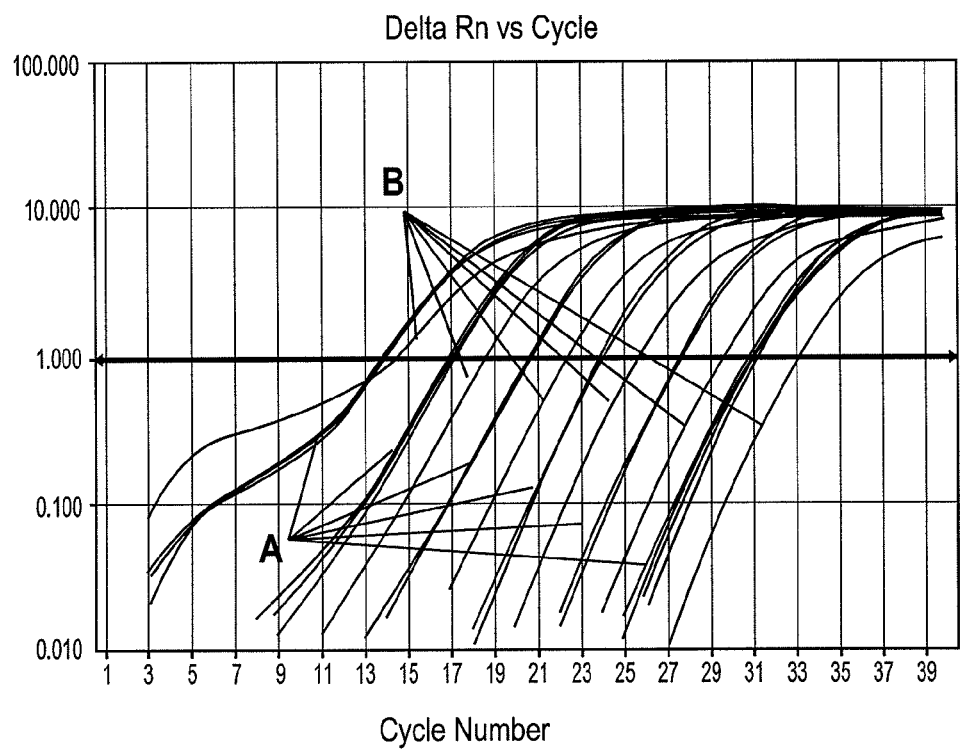
FIG. 5. Performance on AB7500. Compare the same SYBR qPCR supermix (A) and the same control supermix (B) that are used in FIG. 4.

A SYBR Green qPCR mix containing DY-510XL from Dynomics (Germany) and Rox at a low concentration was also tested. The qPCR performance data on AB 7900, an instrument that employs high Rox concentration for normalization, and on AB7500, an instrument that employs low Rox concentration for normalization are shown in FIG. 4 and FIG. 5, respectively.

EXAMPLE 2

A probe-based qPCR mix has been developed that can be used on all real-time instrument platforms including the ones that employ high concentration of passive reference dye. The mixture contains a fluorescent dye with a long Stokes-shift mixed with a low concentration of passive reference dye. In a particular embodiment developed, DY510-XL, the long Stokes-shift dye, is excited at a wavelength that is similar to fluorescein, and emits fluorescence signal in the wavelength range (e.g. ~628 nm) that is similar to the passive reference dye, ROX (e.g. ~590 nm). This example demonstrates that the use of combination of the passive reference dye (i.e. Rox) and the long stokes-shift dye mixed with a pre-formulated qPCR mix, can improve the reproducibility of replicate qPCR reactions on a high-Rox instrument as reflected by the improvement of the standard deviation upon applying Rox normalization (See Table 1). 96 identical qPCR reactions were set up on an AB7900 (high-Rox instrument) using pre-mixes that contain the appropriate amount of the passive reference dye and the long stokes-shift dye along with all other necessary reagents to support PCR amplification. The average Ct values and the standard deviation were determined by analyzing the data with Rox normalization function of the software turned off or turned on. The standard deviation is improved from 0.16 cycles to 0.09 cycles with the use of Rox normalization, which in this case relies on the second passive reference dye that has a long Stokes-shift.

TABLE 1

Improvement of amplification reproducibility

|  | Rox normalization | Average Ct | Standard Deviation |
|---|---|---|---|
| AB 7900 | off | 21.9 | 0.16 |
| (High-Rox instrument) | on | 22.2 | 0.09 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A reaction mixture for signal normalization in a real-time polymerase chain reaction (PCR) amplification of a target nucleic acid wherein the mixture is compatible, without further addition of reagents aside from a sample to be tested and optionally primers, for use in both (a) a high concentration passive dye normalization real-time PCR amplification system and (b) a low concentration passive dye normalization real-time PCR amplification system, wherein the mixture comprises a plurality of passive reference dyes that produces fluorescent signals independent of the amplification reactions.

2. The mixture of claim 1, the mixture comprising
a first passive reference dye having a Stokes-shift, wherein the first passive reference dye is at a concentration sufficient for use in low concentration passive reference dye normalization, wherein the first passive reference dye has a first passive reference dye excitation wavelength maximum and a first passive reference dye emission wavelength maximum; and
a second passive reference dye having a Stokes-shift that is greater than the Stokes-shift of the first passive reference dye, wherein the second passive reference dye has an emission wavelength maximum approximately the same as the first passive reference dye emission wavelength maximum, and an excitation wavelength maximum significantly different than the first passive reference dye excitation wavelength maximum.

3. The mixture of claim 2, wherein the second passive reference dye has a Stokes-shift of at least about 60 nm.

4. The mixture of claim 2, wherein the first passive reference dye comprises 5- and/or 6-carboxy-X-rhodamine, or an analog thereof.

5. The mixture of claim 2, wherein the second passive reference dye has a excitation wavelength maximum of 550 nm or less.

6. The mixture of claim 2, wherein the concentration of the 5- and/or 6-carboxy-X-rhodamine dye is less than 100 nM.

7. The mixture of claim 1, further comprising one or more of an oligonucleotide primer.

8. The mixture of claim 7, comprising DNA polymerase.

9. The mixture of claim 8, wherein the polymerase is complexed with an antibody.

10. The mixture of claim 8, wherein the polymerase is chemically inactivated but is activated by heating.

11. The mixture of claim 2, wherein said second passive dye is a fluorescent dot.

12. The mixture of claim 2, wherein the second passive reference dye is conjugated to a moiety.

13. A method of performing a real-time quantitative polymerase chain reaction, the method comprising,
performing a polymerase chain reaction (PCR) with the mixture of claim 1, wherein the mixture further comprises a biological sample suspected of comprising a target nucleic acid.

14. A method of making the reaction mixture of claim 1, the method comprising mixing the plurality of passive reference dyes, thereby generating the reaction mixture.

15. The mixture of claim 2, wherein the second passive reference dye has an emission wavelength maximum within 30 nm of the first passive reference dye emission wavelength maximum.

16. The mixture of claim 1, the mixture comprising
a first passive reference dye having a Stokes-shift, wherein the first passive reference dye is at a concentration sufficient for use in low concentration passive reference dye normalization, wherein the first passive reference dye has a first passive reference dye excitation wavelength maximum and a first passive reference dye emission wavelength maximum and wherein the first passive reference dye comprises 5- and/or 6-carboxy-X-rhodamine, or an analog thereof; and
a second passive reference dye having a Stokes-shift that is greater than the Stokes-shift of the first passive reference dye, wherein the second passive reference dye has an emission wavelength maximum within 30 nm of the first passive reference dye emission wavelength maximum, and an excitation wavelength maximum of 550 nm or less.

17. The mixture of claim 16, wherein the second passive reference dye has an emission wavelength maximum of 590-630 nm and an excitation wavelength maximum of 470-510 nm.

18. The mixture of claim 1, further comprising a reverse transcriptase.

* * * * *